United States Patent
Thorsteinsson et al.

(10) Patent No.: US 9,724,210 B2
(45) Date of Patent: Aug. 8, 2017

(54) PROSTHETIC AND ORTHOTIC DEVICES HAVING MAGNETORHEOLOGICAL ELASTOMER SPRING WITH CONTROLLABLE STIFFNESS

(71) Applicant: Össur hf, Reykjavik (IS)

(72) Inventors: Freygardur Thorsteinsson, Reykjavik (IS); Ivar Gudmundsson, Reykjavik (IS); Christophe Lecomte, Reykjavik (IS)

(73) Assignee: Össur hf, Reykjavik (IS)

( * ) Notice: Subject to any disclaimer, the term of this patent is extended or adjusted under 35 U.S.C. 154(b) by 9 days.

(21) Appl. No.: 14/714,575

(22) Filed: May 18, 2015

(65) Prior Publication Data
US 2015/0245927 A1 Sep. 3, 2015

Related U.S. Application Data

(63) Continuation of application No. 13/604,444, filed on Sep. 5, 2012, now Pat. No. 9,078,734.
(Continued)

(51) Int. Cl.
*A61F 2/50* (2006.01)
*A61F 2/66* (2006.01)
(Continued)

(52) U.S. Cl.
CPC .............. *A61F 2/6607* (2013.01); *A61F 2/66* (2013.01); *A61F 5/0102* (2013.01);
(Continued)

(58) Field of Classification Search
CPC ...... A61F 2/60; A61F 2/66; A61F 2/70; A61F 2002/5003; A61F 2002/5004;
(Continued)

(56) References Cited

U.S. PATENT DOCUMENTS

| 5,486,209 A | 1/1996 | Phillips |
| 5,514,186 A | 5/1996 | Phillips |

(Continued)

FOREIGN PATENT DOCUMENTS

| CN | 101450016 | 6/2009 |
| EP | 0706189 A1 | 4/1996 |

(Continued)

OTHER PUBLICATIONS

Carlson, J. D., et al, "MR fluid, foam and elastomer devices", Mechatronics, Jun. 1, 2000, pp. 555-569, vol. 10, No. 4-5, Pergamon Press, Oxford, GB.

(Continued)

*Primary Examiner* — Thomas J Sweet
*Assistant Examiner* — Christie Bahena
(74) *Attorney, Agent, or Firm* — Knobbe, Martens, Olson & Bear, LLP

(57) ABSTRACT

A prosthetic or orthotic device includes a body configured to support at least a portion of a human limb of a user wearing the prosthetic or orthotic device. The device can also include a shock absorption member coupled to the body. The shock absorption member includes one or more magnetorheological elastomer (MRE) springs disposed between a first portion of the body and a second portion of the body. The one or more MRE springs are selectively actuatable to vary a stiffness of the shock absorption member via the application of a magnetic flux, thereby adjusting a stiffness of the body of the prosthetic or orthotic device to a level corresponding to an activity level of the user.

12 Claims, 9 Drawing Sheets

Related U.S. Application Data

(60) Provisional application No. 61/531,492, filed on Sep. 6, 2011.

(51) Int. Cl.
*A61F 2/70* (2006.01)
*A61F 5/01* (2006.01)
*A61F 2/76* (2006.01)
*A61F 5/11* (2006.01)
*A61F 2/68* (2006.01)
*A61B 5/11* (2006.01)

(52) U.S. Cl.
CPC ..... *A61B 5/1118* (2013.01); *A61F 2002/5003* (2013.01); *A61F 2002/503* (2013.01); *A61F 2002/5004* (2013.01); *A61F 2002/5007* (2013.01); *A61F 2002/5009* (2013.01); *A61F 2002/5033* (2013.01); *A61F 2002/5072* (2013.01); *A61F 2002/6614* (2013.01); *A61F 2002/6678* (2013.01); *A61F 2002/6863* (2013.01); *A61F 2002/704* (2013.01); *A61F 2002/707* (2013.01); *A61F 2002/764* (2013.01); *A61F 2002/7635* (2013.01)

(58) Field of Classification Search
CPC ...... A61F 2002/5007; A61F 2002/5033; A61F 2002/5072; A61F 2002/6614; A61F 2002/6683; F16F 1/361
See application file for complete search history.

(56) References Cited

U.S. PATENT DOCUMENTS

| | | |
|---|---|---|
| 6,443,993 B1 | 9/2002 | Koniuk |
| 6,478,826 B1 | 11/2002 | Phillips et al. |
| 6,511,512 B2 | 1/2003 | Phillips et al. |
| 6,610,101 B2 | 8/2003 | Herr et al. |
| 6,764,520 B2 | 7/2004 | Deffenbaugh et al. |
| 6,887,279 B2 | 5/2005 | Phillips et al. |
| 7,029,500 B2 | 4/2006 | Martin |
| 7,101,487 B2 | 9/2006 | Hsu et al. |
| 7,169,190 B2 | 1/2007 | Phillips et al. |
| 7,198,071 B2 | 4/2007 | Bisbee et al. |
| 7,393,364 B2 | 7/2008 | Martin |
| 7,431,737 B2 | 10/2008 | Ragnarsdottir et al. |
| 7,455,696 B2 | 11/2008 | Bisbee et al. |
| 7,598,651 B2 | 10/2009 | Kornbluh et al. |
| 7,598,652 B2 | 10/2009 | Kornbluh et al. |
| 7,691,154 B2 | 4/2010 | Asgeirsson et al. |
| 7,766,974 B2 | 8/2010 | Curtis |
| 7,856,741 B2 | 12/2010 | Nguyen et al. |
| 8,820,492 B1 | 9/2014 | Kavlicoglu et al. |
| 9,078,734 B2 | 7/2015 | Thorsteinsson et al. |
| 9,265,626 B1 | 2/2016 | Lecomte et al. |
| 2003/0120353 A1 | 6/2003 | Christensen |
| 2005/0038525 A1 | 2/2005 | Doddroe et al. |
| 2005/0216098 A1 | 9/2005 | Christensen |
| 2005/0283257 A1 | 12/2005 | Bisbee et al. |
| 2006/0136072 A1 | 6/2006 | Bisbee et al. |
| 2007/0043449 A1 | 2/2007 | Herr et al. |
| 2009/0133976 A1 | 5/2009 | Bose et al. |
| 2009/0299480 A1 | 12/2009 | Gilbert et al. |
| 2010/0193304 A1 | 8/2010 | Bose et al. |
| 2010/0314842 A1 | 12/2010 | Rodenbeck |

FOREIGN PATENT DOCUMENTS

| | | |
|---|---|---|
| WO | WO 2009/099352 | 8/2009 |
| WO | WO 2013/055462 A1 | 4/2013 |

OTHER PUBLICATIONS

Dong, Xiao-Min, et al., "A new variable stiffness absorber based on magneto-rheological elastomer", Transactions of Nonferrous Metals Society of China, Dec. 1, 2009, pp. s611-s615, vol. 19, Science China Press, Beijing, CN.

Ginder et al., "Controllable-Stiffness Components Based on Magnetorheological Elastomers", 2000, Smart Structures and Smart Materials, vol. 3985.

Ginder, J. M., et al, "Magnetorheological Elastomers: Properties and Applications", Proceedings of SPIE Conference on Smart Materials Technologies, Mar. 1, 1999, pp. 131-138, vol. 3675, SPIE—The International Society for Optical Engineering, US.

Li et al., "Development of an Intelligent Prosthetic Ankle Joint", 2$^{nd}$ Report, Development of the 1$^{st}$ Prototype with Intelligent Prosthetic Ankle Joint, 2005, Graduate School of Engineering, Osaka University.

Li, Weihua and Xianzhou Zhang, Research and Applications of MR Elastomers, Recent Patents on Mechanical Engineering, Sep. 18, 2008, 161-166, vol. 1-3, Bentham Science Publishers, Ltd.

Lerner, A. Albanese and K.A. Cunefare, Performance of MRE-based Vibration Absorbers, Journal of Intelligent Material Systems and Structures, May 2008, 551-563, vol. 19, Sage Publications.

Search Report and Written Opinion in corresponding International Patent Application No. PCT/US2012/053802, mailed Feb. 15, 2013.

Extended Search Report in corresponding European Application No. 12839404.6, dated Apr. 13, 2015.

International Preliminary Report on Patentability in corresponding International Patent Application No. PCT/US2012/053802, mailed Mar. 20, 2014.

Endolite elite blade VT product brochure, http://www.endolite.co.uk/products/feet/eliteblade/eliteblade_foot.html, available before May 31, 2011.

Össur Ceterus product; Ossur Prosthetics Product Catalog, pp. 204-212, 2005.

Össur Re-Flex Rotate product, catalog pages available at http://www.ossur.com/?PageID=15418, announced on website Nov. 2010.

Össur Re-Flex VSP product, Ossur Prosthetics Product Catalog, pp. 187-194, 2005.

US 9,724,210 B2

PROSTHETIC AND ORTHOTIC DEVICES HAVING MAGNETORHEOLOGICAL ELASTOMER SPRING WITH CONTROLLABLE STIFFNESS

CLAIM FOR PRIORITY

The present application is a continuation of U.S. application Ser. No. 13/604,444, filed Sep. 5, 2012, which claims priority benefit under 35 U.S.C. §119(e) to U.S. Provisional Patent Application Ser. No. 61/531,492, filed Sep. 6, 2011, the entire contents of both are incorporated by reference and should be considered a part of this specification.

BACKGROUND

Field

The present application relates in certain embodiments to prosthetic and orthotic devices. In particular, the present application in certain embodiments relates to prosthetic and orthotic device with one or more magnetorheological (MR) elastomer springs having a controllable stiffness.

Description of the Related Art

Conventional prosthetic and orthotic devices seek to approximate the feel and fluid range of motion of a human limb's natural movement, such as the natural stride of a human foot. Additionally, prosthetic and orthotic devices seek to provide the appropriate level of stiffness for the user, based on the activity level of the user. High stiffness is required in more demanding activities (e.g., running, jumping), while low stiffness is required for comfort while at rest or moving casually (e.g., walking). However, the components in conventional orthotic and prosthetic devices (e.g., prosthetic foot plates and heel plates) generally have a set or fixed stiffness, regardless of the activity level of the user.

Accordingly, there is a need for orthotic and prosthetic devices where the stiffness of the device is controllable and adaptable to the user's activity level, and capable of being controlled either manually or automatically by responding to signals that represent the current activity level of the user, where the operating characteristics of the device can be changed in real-time.

SUMMARY

In accordance with one embodiment, orthotic and prosthetic devices are provided where the stiffness of the device is controllable and adaptable to the user's current activity level, so the stiffness of the device changes with a change in the user's activity level, and capable of changing the stiffness characteristics of the device in real time. In one embodiment, the stiffness of the device is controlled manually by the user. In another embodiment, the stiffness of the device is controlled automatically (e.g. via a computer processor) by responding to signals that represent the current activity level of the user.

In accordance with one embodiment, a prosthetic or orthotic device is provided comprising a body configured to support at least a portion of a human limb of a user wearing the prosthetic or orthotic device. The device further comprises a shock absorption member coupled to the body. The shock absorption member comprises one or more magnetorheological elastomer (MRE) springs disposed between a first portion of the body and a second portion of the body. The one or more MRE springs are selectively actuatable to vary a stiffness of the shock absorption member via the application of a magnetic flux, thereby adjusting a stiffness of the body of the prosthetic or orthotic device to a level corresponding to an activity level of the user.

In accordance with another embodiment, a prosthetic foot is provided. The prosthetic foot comprises a foot plate extending from a proximal portion to a generally horizontal distal portion, the foot plate curving generally downwardly and forwardly between the proximal and distal portions. The prosthetic foot also comprises an adapter coupled to the proximal portion of the foot plate. The prosthetic foot further comprises a shock absorbing member removably coupled to the adapter. The shock absorbing member comprises a cylindrical core extending along a generally vertical axis and an electrically conducting coil disposed about the cylindrical core. The shock absorbing member further comprises a spring surrounding the core and the coil, the spring comprising a magnetorheological elastomer (MRE) material. The MRE spring is actuatable to vary the stiffness of the shock absorbing member via the application of a magnetic flux to the spring.

DETAILED DESCRIPTION

Figure 1A:
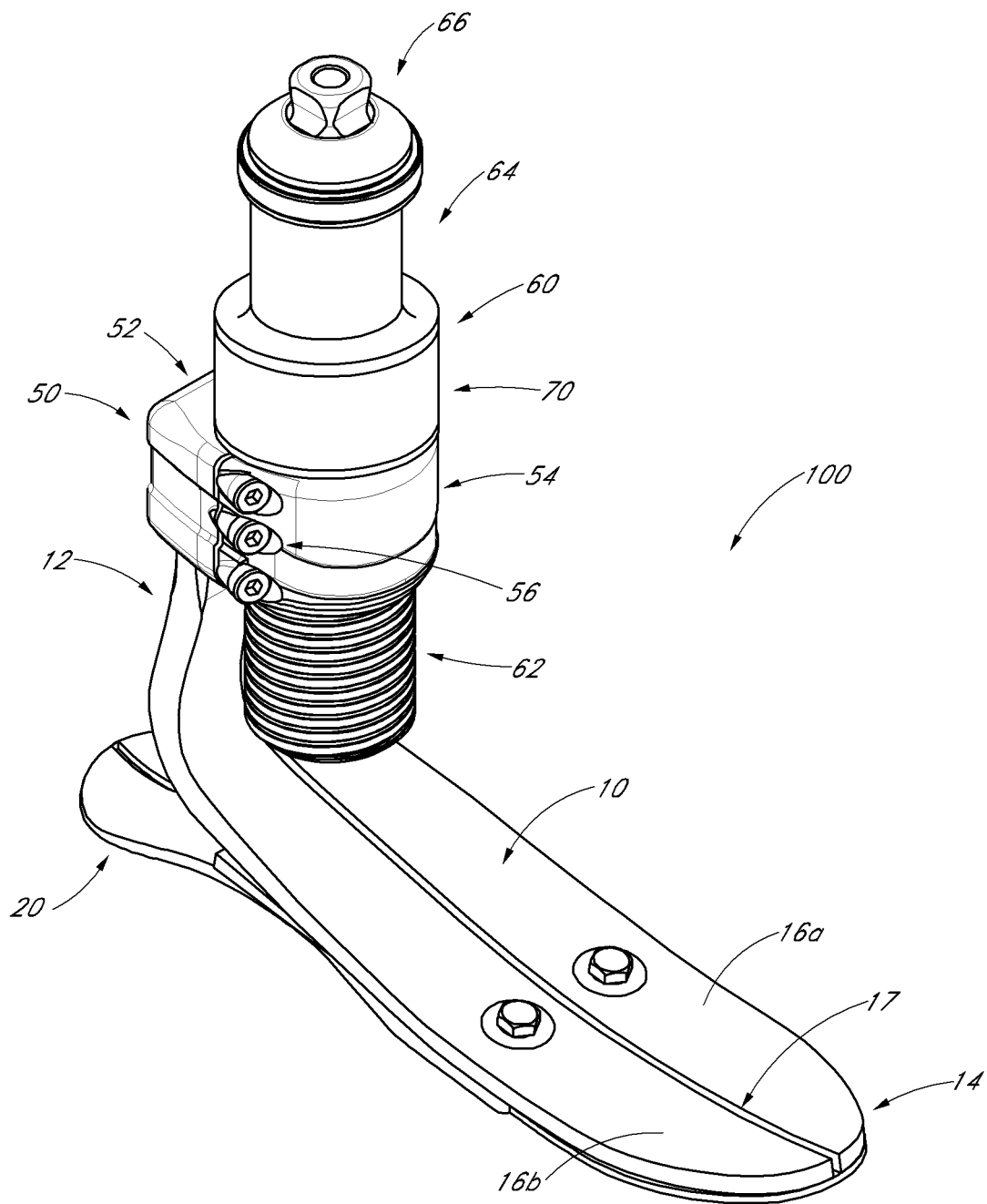
FIG. 1A is a schematic perspective view of one embodiment of a prosthetic foot with a magnetorheological elastomer (MRE) spring.

Described below are embodiments of prosthetic and orthotic devices having a magnetorheological elastomer spring with controllable stiffness (hereinafter "MRE spring"). The stiffness and related mechanical properties of the MRE spring can be changed rapidly and reversibly by inducing a magnetic flux through the MRE spring. The magnetic flux required to change the stiffness of the spring is generated by other structures within the device that are magnetized in response to an externally applied electrical current through a coil.

In some embodiments, the prosthetic or orthotic device can operate at more than one level of stiffness and other related mechanical properties so that it adapts to the user's activity level. For example, a relatively higher stiffness may be desired in more demanding tasks (e.g., running, jumping) while a relatively lower stiffness is desired for comfort while at rest or moving casually (e.g., walking). In some embodiments, the user may control the stiffness of the MRE spring manually (e.g., by pressing a button, actuating a lever) to apply an electrical current or voltage in response to changing intensity of the activity level. In another embodiment, the user can control the stiffness of the MRE spring remotely, for example via a hand held remote control that communicates wirelessly with a receiver in the prosthetic or orthotic device (e.g., via an Rf communication system). In another embodiment, the stiffness of the MRE spring can be controlled automatically (e.g., via a computer processor) in response to some input signal based on the user's activity. For example, one or more sensors (e.g., as a force sensor) can be provided in the prosthetic or orthotic device to sense one or more parameter (e.g., the amount of force being applied by the user) during ambulation, and based on the sensed parameter (s), a controller can determine (e.g., using one or more control algorithms) whether the user is in a low activity level or a high activity level, and apply an electrical current or voltage to the MRE spring to provide a corresponding level of stiffness.

In one embodiment, the disclosed magnetorheological elastomers (MREs) comprise ferromagnetic particles interspersed within an elastomer matrix, whose resulting properties such as stiffness changes dynamically in response to a magnetic flux (e.g., when subjected to a magnetic field, so that the MRE changes in stiffness, such as from relatively low to high stiffness, substantially instantaneously). For example, in one embodiment a MRE may comprise magnetizable carbonyl iron particles embedded in silicone, polyurethane or natural rubber. MREs may be produced by mixing magnetizable particles with an uncured elastomer, and subsequently curing the compound in a mold under the presence of a magnetic flux. The presence of the magnetic flux induces the ferromagnetic particles having magnetic dipoles to form columnar chains of ferromagnetic particles. The degree of the chain formation and the particle density are proportional to the magnitude of the change in stiffness the resulting MRE can display. For example, having a high density of ferromagnetic particles and a high level of chain formation results in a higher stiffness of the MRE under a magnetic flux compared to the stiffness without the magnetic flux.

Figure 1B:
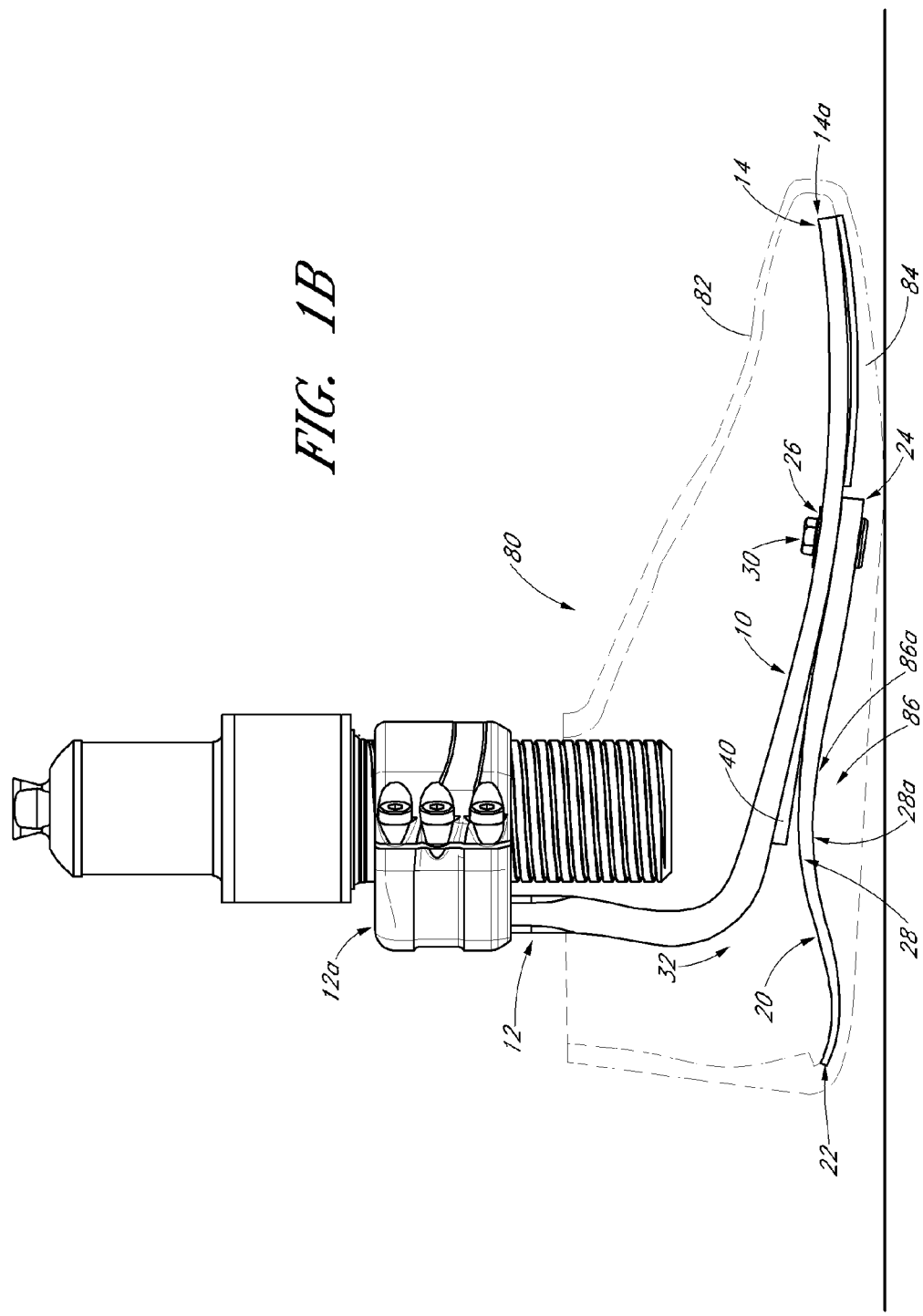
FIG. 1B is a schematic side view of the prosthetic foot of FIG. 1A disposed in a cosmesis foot cover (shown in cross-section).

FIGS. 1A-1B show one embodiment of a prosthetic foot 100 with a MRE spring. The prosthetic foot 100 can have a foot member 10 that extends from a proximal section 12 to a distal section 14. In the illustrated embodiment, the proximal section 12 can be generally vertically oriented, and the distal section 14 be generally horizontally oriented with the foot member 10 curving downward from the proximal section 12 to the distal section 14. The proximal section 12 can extend to a proximal end 12a and be generally at a location of a natural human ankle. In one embodiment, the distal section 14 can extend to a distal end 14a generally at a location of natural human toes.

With continued reference to FIGS. 1A-1B, the foot member 10 can have multiple elongate segments that can flex independently relative to each other. In the illustrated embodiment, the foot member 10 has two elongate segments 16a, 16b that are separated from each other by a slot 17 that extends along a length between the distal end 14a and the proximal end 12a of the foot member 10. In one embodiment, the slot extends along the entire length of the foot member 10. In another embodiment, the slot 17 extends along a length that is shorter than the entire length of the foot member 10. In one embodiment, the slot 17 extends linearly along its length, so that the width of all the elongate segments 16a, 16b is generally the same. In another embodiment, the slot 17 can have a curved section, such that one of the elongate segments has a different width than another of the elongate segments over at least a portion of their lengths. In still another embodiment, the foot member 10 can have multiple slots 17 between multiple elongate segments.

The prosthetic foot 100 can also have a heel member 20 that extends between a proximal end 22 and a distal end 24 and is disposed below at least a portion of the foot member 10. In one embodiment, the heel member 20 can be coupled to the foot member 10 via one or more fasteners 30 (e.g., bolts) at a location between the proximal and distal ends 12a, 14a of the foot member 10 such that the heel member is cantilevered relative to the foot member 10 and extends to a free rear end at the proximal end 22. The heel member 20 can have a curvilinear profile along its length that defines an arch 28 between the proximal and distal ends 22, 24. As best seen in FIG. 1B, the foot and heel members 10, 20 can define a slot 32 in the fore-aft direction at a rear portion of the prosthetic foot 100. In one embodiment, the slot 32 can taper toward a front end of the prosthetic foot 100. A resilient member 40 can be interposed between the heel member 20 and the foot member 10 within the slot 32. In one embodiment, the resilient member 40 can separate at least a portion of the foot member 10 from the heel member 20. In another embodiment, the resilient member 40 can completely separate the foot member 10 from the heel member 20.

In one embodiment, the foot and heel members 10, 20 are plate-like members with generally planar top and bottom surfaces. The foot and heel members 10, 20 can be made of lightweight resilient materials, such as graphite, fiberglass, carbon fiber and the like. In some embodiments, the foot and heel members 10, 20 can formed of multiple layers of material that define a monolithic piece.

The prosthetic foot 100 can also have a connector 50 that attaches to the proximal section 12 of the foot member 10. In one embodiment, the connector 50 can have a recess at a rear portion 52 thereof that fits over the proximal section 12 of the foot member 10. In one embodiment, the connector 50 can be attached to the foot member 10 by an adhesive (e.g., delivered into the recesses to bond the connector 50 to the proximal section 12 of the foot member 10). In another embodiment, the connector 50 can be coupled to the foot member 10 with one or more fasteners (e.g., threaded fasteners).

With continued reference to FIGS. 1A-1B, the prosthetic foot 100 can have a shock absorbing module 60 that couples to a front portion 54 of the connector 50. In one embodiment, the shock absorbing module 60 can have a threaded distal section 62 that threadably couples to an inner threaded surface (not shown) of the front portion 54 to couple the module 60 to the connector 50, and one or more fasteners 56 can be adjusted to lock the shock module 60 relative to the connector 50 to fix the axial position of the module 60. The shock module 60 can also have a proximal portion 64 that extends above the connector 50, and an adapter 66 at its proximal end. In the illustrated embodiment, the adapter 66 is a male pyramid adapter. However, in other embodiments, the adapter 66 can be a tube connector. The shock absorbing module 60 can also include a spring module 70 between the adapter 66 and the connector 50 that includes a MRE spring, and is further described below.

As shown in FIG. 1B, the prosthetic foot 100 can be coupled (e.g., removably coupled) to a cosmesis foot cover 80 that has an upper portion 82 and a sole portion 84. In one embodiment, the sole portion 84 can have an insole portion 86 with a convex surface 86a that corresponds to the curvature of a concave bottom surface 28a of the arch 28 of the heel member 20, such that the insole portion 86 maintains contact with the bottom surface 28a of the heel member 20 during ambulation of the prosthetic foot 100 from heel strike to toe-off.

Figure 1C:
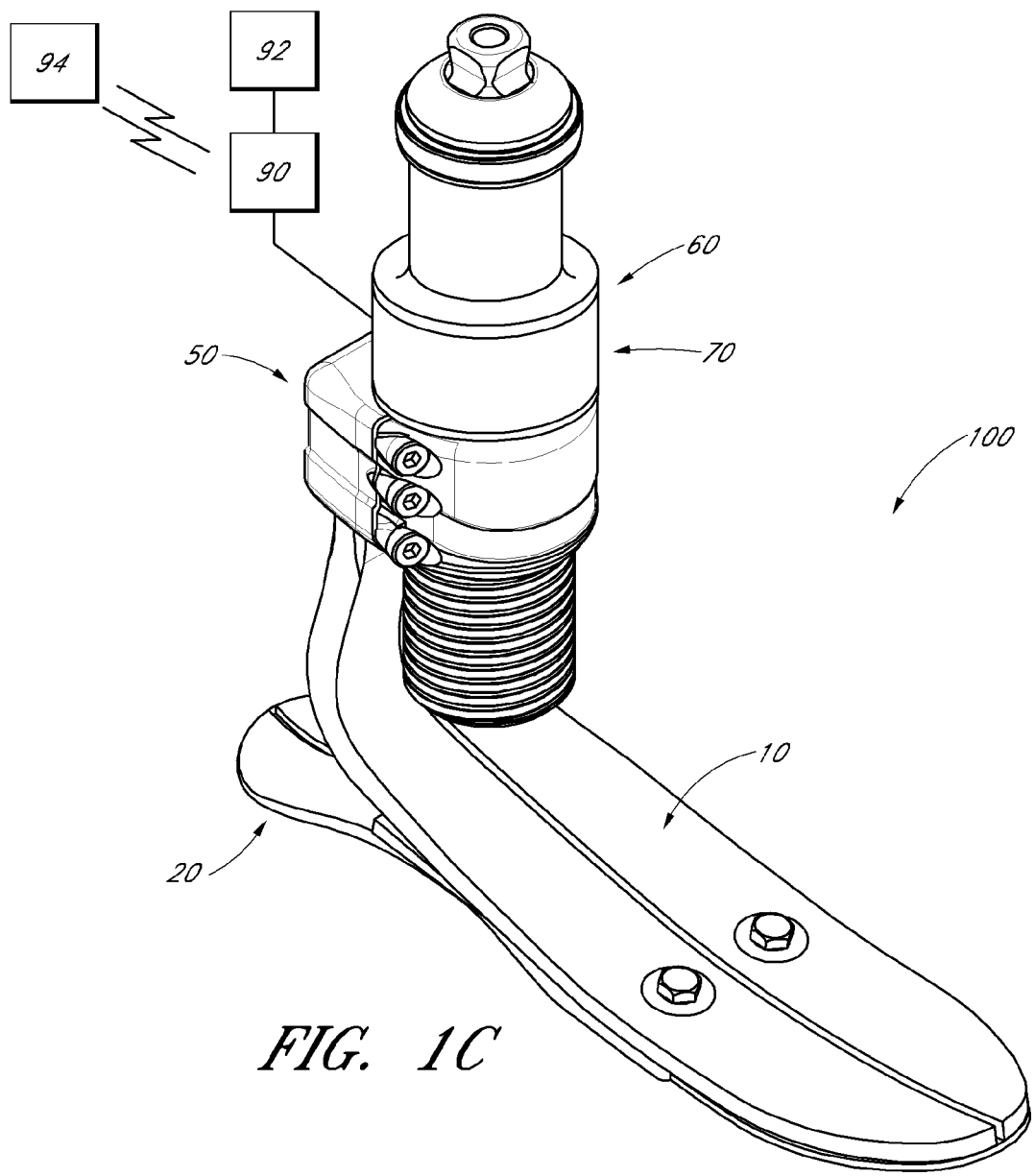
FIG. 1C is a schematic perspective view of another embodiment of the prosthetic foot in FIG. 1A.

FIG. 1C shows another embodiment of the prosthetic foot 100 having a switch 90 electrically connected to an electrical power source 92 (e.g., battery). In one embodiment, the switch 90 and/or power source 92 can be attached to the prosthetic foot 100. In one embodiment, the switch 90 can be manually actuated by the user (e.g., by pressing a button or turning a lever) to apply a current to the spring module 70 to change the stiffness of the shock module 60. In another embodiment, the switch 90 can be an electrical switch and can be actuated remotely via a remote control 94 (e.g., hand held remote control), which can be used by the user to remotely control the stiffness of the spring module 70 (e.g., using RF communication communicated by the remote control 94 to a wireless receiver in the switch 90).

Figure 1D:
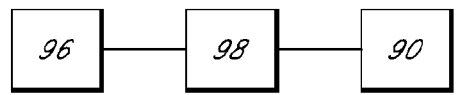
FIG. 1D is a schematic view of a control system for the prosthetic foot of FIG. 1A.

In another embodiment, shown in FIG. 1D, a controller 98 (e.g., electronic controller, computer controller) can automatically control the stiffness of the spring module 70 of the shock module 60 based on sensed information received during ambulation (e.g., sensed information received from the prosthetic foot 100). For example, the prosthetic foot 100 can have one or more sensors 96 (e.g., force sensors, pressure sensors, accelerometers) that can sense one or more parameters associated with ambulation (e.g., level of force or acceleration exerted by the user) during use of the prosthetic foot 100. The sensors 96 can communicate signals indicative of such parameters to the controller 98, which can then operate the switch 90 to apply a current to the spring module 70 to change the stiffness of the shock module 60 (e.g., using one or more control algorithms stored on a memory that can be accessed by the controller 98) based on the sensed parameter information. For example, if the one or more sensors 96 sense a force and/or acceleration above a first threshold, the controller 98 can operate the switch 90 to apply a current to the spring module 70 to increase the stiffness of the shock module 60. Similarly, if the one or more sensors 96 sense a force and/or acceleration below a second threshold (which can in one embodiment be generally equal to the first threshold), the controller 98 can operate the switch 90 to not apply current (or apply a reduced current) to the spring module 70 to decrease the stiffness of the shock module 60. In one embodiment, the one or more sensors 96 can be positioned on a load bearing surface of the prosthetic foot 100 (e.g., one the heel member 20 and/or the foot member 10). In one embodiment, the controller 98 can be disposed on the prosthetic foot 100.

Further details on prosthetic feet can be found in U.S. Publication 2005/0038524, U.S. Pat. No. 7,846,213, U.S. application Ser. No. 13/034,474, filed Feb. 24, 2011 and titled "Prosthetic Foot with a Curved Split," and U.S. application Ser. No. 13/149,118, filed May 31, 2011 and titled "Height-adjustable Threaded Shock Absorbing Module and Associated Coupling Member," the entire contents of all of which are hereby incorporated by reference and should be considered a part of this specification. Further details of foot covers and insole portions can be found in US Publication 2010/0004757 titled "Smooth Rollover Insole for Prosthetic Foot" and US Publication 2006/0015192 titled "Functional Foot Cover," the entire contents of all of which are hereby incorporated by reference and should be considered a part of this specification.

Figure 2:
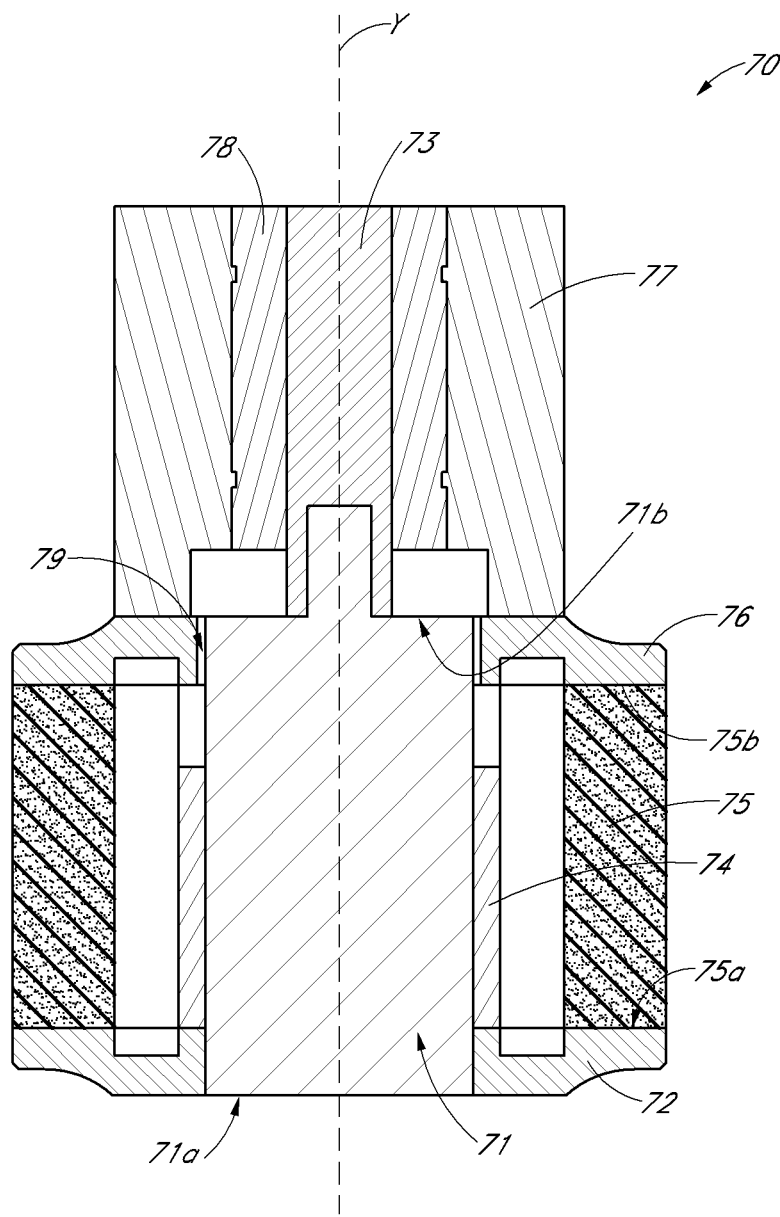
FIG. 2 is a schematic cross-sectional side view of one embodiment of a shock absorber having a MRE spring.

FIG. 2 shows a cross sectional structural view of one embodiment of the spring module 70 of the shock absorbing module 60. Disposed along a vertical axis Y on the lower portion of the spring module 70 is a cylindrical core 71 (hereinafter "core") comprising a magnetizable material. An example of a magnetizable material is Vacoflux™, which is an Fe—Co alloy. However, other suitable magnetizable materials can be used. The core 71 is connected to a magnetizable lower disc 72 (e.g., made of Vacoflux™) on the bottom end 71a, and a non-magnetizable rod 73 on the upper end 71b. The rod 73 can be made, for example, out of aluminum. However, the rod 73 can be made of other suitable non-magnetizable materials. The core 71 can also be connected on the bottom to a structural member, such as the threaded distal section 62 of the shock absorbing module 60 (see FIG. 1). In another embodiment, the core 71 can be connected at its bottom end 71a to an adapter, such as a pyramid adapter of a prosthetic device.

Disposed around the vertical axis Y and surrounding the core 71 can be a coil 74 that can be actuated to induce a magnetic flux having a magnitude sufficient to magnetize surrounding magnetizable structures, including the core 71, in response to an applied current. In one embodiment, said current can be applied by a power source, such as a battery, that can be external to the shock absorbing module 60. In another embodiment, the power source can be coupled to, or housed in the shock absorbing module assembly.

With continued reference to the embodiment in FIG. 2, an MRE spring 75 can be disposed around, and housing, both the core 71 and the coil 74. In the illustrated embodiment, the MRE spring 75 is a hollow cylinder (e.g., cylinder with an annulus) made of a MRE material. In another embodiment, the MRE spring 75 can be a solid piece (e.g., not annular) that is disposed generally parallel to the core 71. The MRE spring 75 can be disposed between a magnetizable upper disc 76 (e.g., made of Vacoflux™) and the magnetizable lower disc 72, and can provide variable elasticity to the spring module 70 depending on whether or not a magnetic flux is directed through the MRE.

The upper disc 76 can be attached to a top end 75b of the MRE spring 75 about the top end 71b of the core 71, and the lower disc 72 can be attached to a bottom end 75a of the MRE spring 75, for example with a suitable adhesive. The upper disc 76 can also be attached to a non-magnetizable housing 77 (e.g., a cylindrical housing) that surrounds the non-magnetizable rod 73. In one embodiment, the housing 77 can be made of aluminum. In another embodiment, the housing 77 can be made of titanium. However, the housing 77 can be made of other suitable non-magnetizable materials. A linear bearing 78 (e.g., linear ball bearing) can be interposed between the rod 73 and the non-magnetizable housing 77 and attached to the housing 77. The bearing 78 advantageously allows and directs the motion of the upper disc 76 relative to the lower disc 76, while keeping the upper disc 76 sufficiently separated (e.g., radially separated) from the core 71 to minimize friction between the core 71 and the upper disc 76. The spacing 79 (e.g. radial gap) between the core 71 and upper disc 76 is kept at minimum to avoid losses in the magnetic circuit. In one embodiment, the spacing 79 is between about 0.1 mm and about 2 mm. In another embodiment, the spacing 79 can be between about 0.1 mm and about 0.2 mm. In still another embodiment, the spacing 79 can be less than about 0.1 mm.

With continued reference to FIGS. 1A-2, during operation of the prosthetic foot 100, an electrical current can be applied to the coil 74 of the spring module 70, thereby inducing a magnetic flux through the core 71, the upper disc 76, and the lower disc 72. The flux magnetizes the core 71, the upper disc 76, and the lower disc 72, which in turn induces a magnetic flux through the MRE spring 75 that effects a change in the stiffness of the MRE spring 75 to a level that is different from the stiffness without the magnetic flux. Upon removal of the applied current, the stiffness of the MRE spring 75 reverts back to the stiffness value that the MRE spring 75 has when the magnetic flux is not present. In one example, the magnetic flux results in a higher level of stiffness of the MRE spring 75 compared to the stiffness without the flux.

Figure 3:
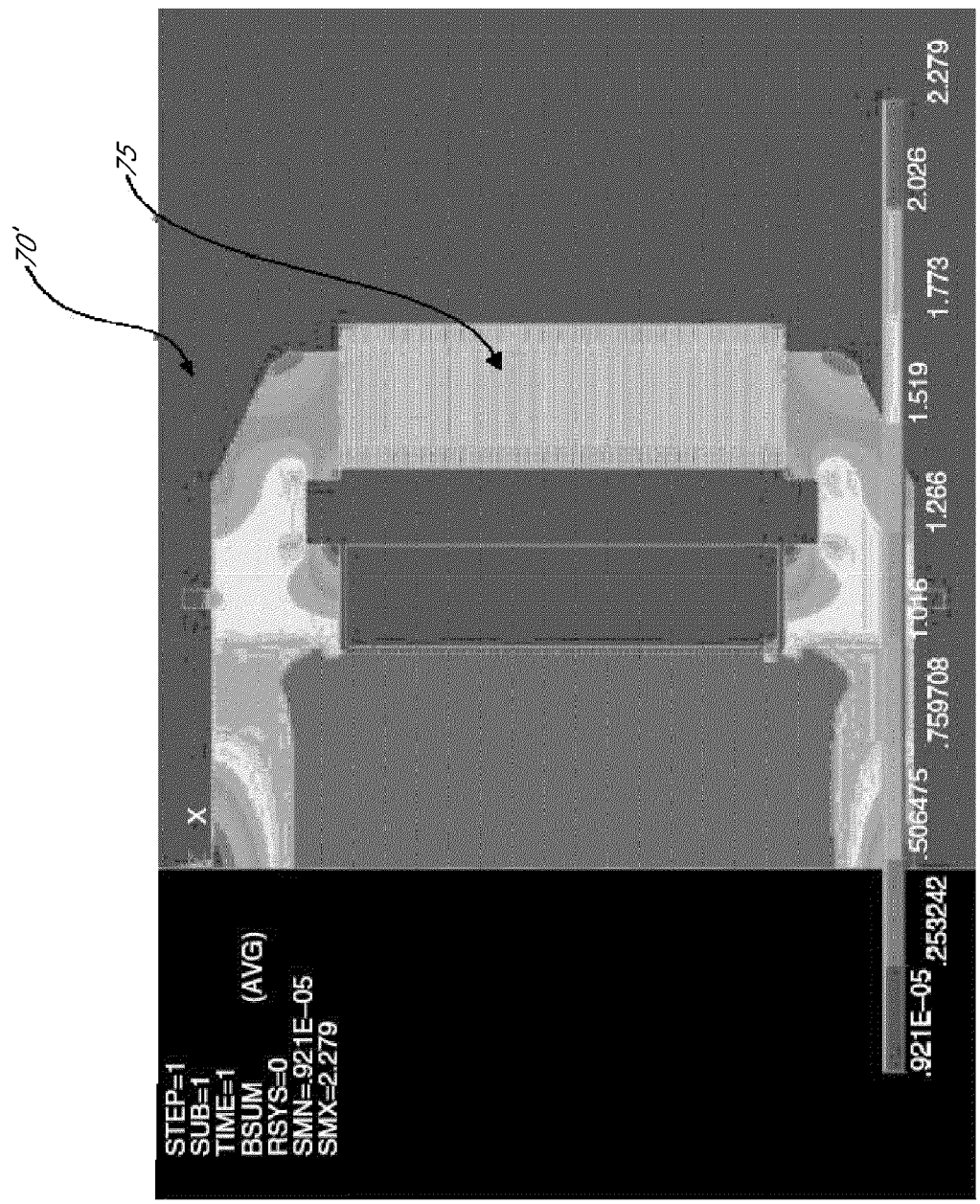
FIG. 3 is a representation of the magnetic flux density in the resulting magnetic circuit of one embodiment of a MRE spring, as computed by an axis-symmetric finite element model of the magnetic circuit.

FIG. 3 shows a representation of the magnetic flux density in the resulting magnetic circuit of one embodiment of a MRE spring module 70', as computed by an axis-symmetric finite element model of the magnetic circuit. In one embodiment, the MRE spring 75 has a magnetic flux density of about 0.6 Tesla. In another embodiment, the MRE spring 75 can have a magnetic flux density greater than 0.6 Tesla (e.g., between 0.6 Tesla and 0.7 Tesla, or greater). In still another embodiment, the MRE spring 75 can have a magnetic flux density less than 0.6 Tesla (e.g., about 0.5 Tesla or between 0.5 Tesla and 0.6 Tesla). In still another embodiment, the MRE spring 75 has a magnetic flux density such that substantial magnetic saturation of the ferromagnetic particles in the MRE composite is achieved. For example, where the MRE spring 75 includes a MRE composite with about 27% iron particles, near complete magnetic saturation of the particles is achieved with a magnetic flux density of about 2.2 Tesla through the iron particles, or a magnetic flux density of about 0.6 Tesla through the MRE spring 75.

Figure 4:
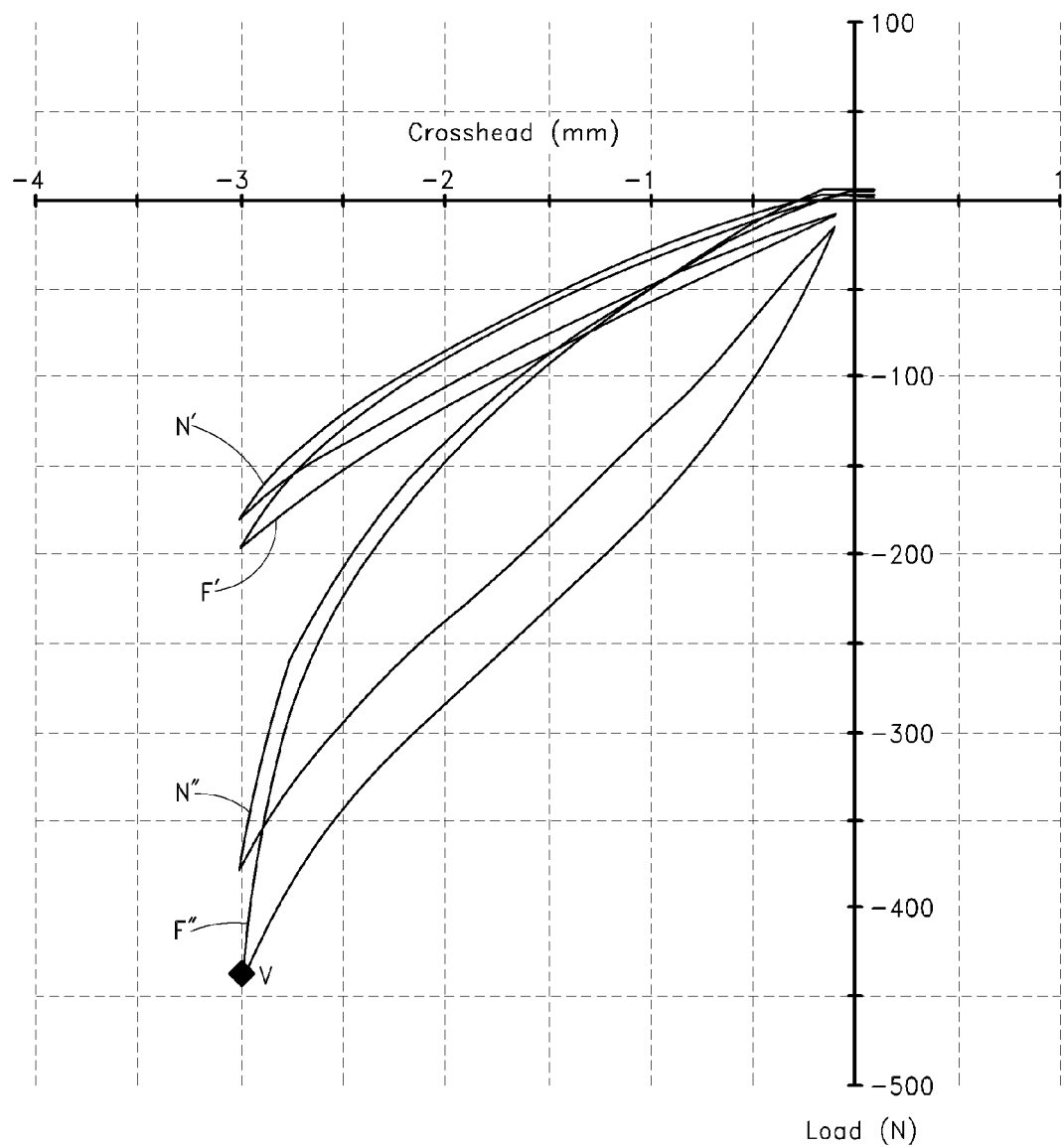
FIGS. 4-4A are graphs showing testing results, showing the spring constant k of a material test sample with a solid cross-section with and without the magnetic flux. The x-axis shows the displacement (in mm) and the y axis shows the force (in N), from which the spring constant can be derived.

FIG. 4 shows testing results, showing a force-displacement curve for two material test samples (e.g., material samples 2 and 6 in Table 4.1 below), with and without a magnetic flux applied to it. Seventeen samples were tested. All test samples were cylindrical with a height of 20 mm, a diameter of 25 mm and a particle concentration of 27% vol./vol, where the particles used were BASF CC or BASF CM carbonyl iron powder. Table 4.1, below shows an overview of the performance of the seventeen samples, where $F_{off}$ is the force needed to effect a given displacement without the magnetic flux, $F_{on}$ is the force needed to effect a given displacement with the magnetic flux applied, $K_{off}$ is the spring constant without the magnetic flux applied, $K_{on}$ is the spring constant when the magnetic flux is applied, and PU is polyurethane.

Figure 4A:
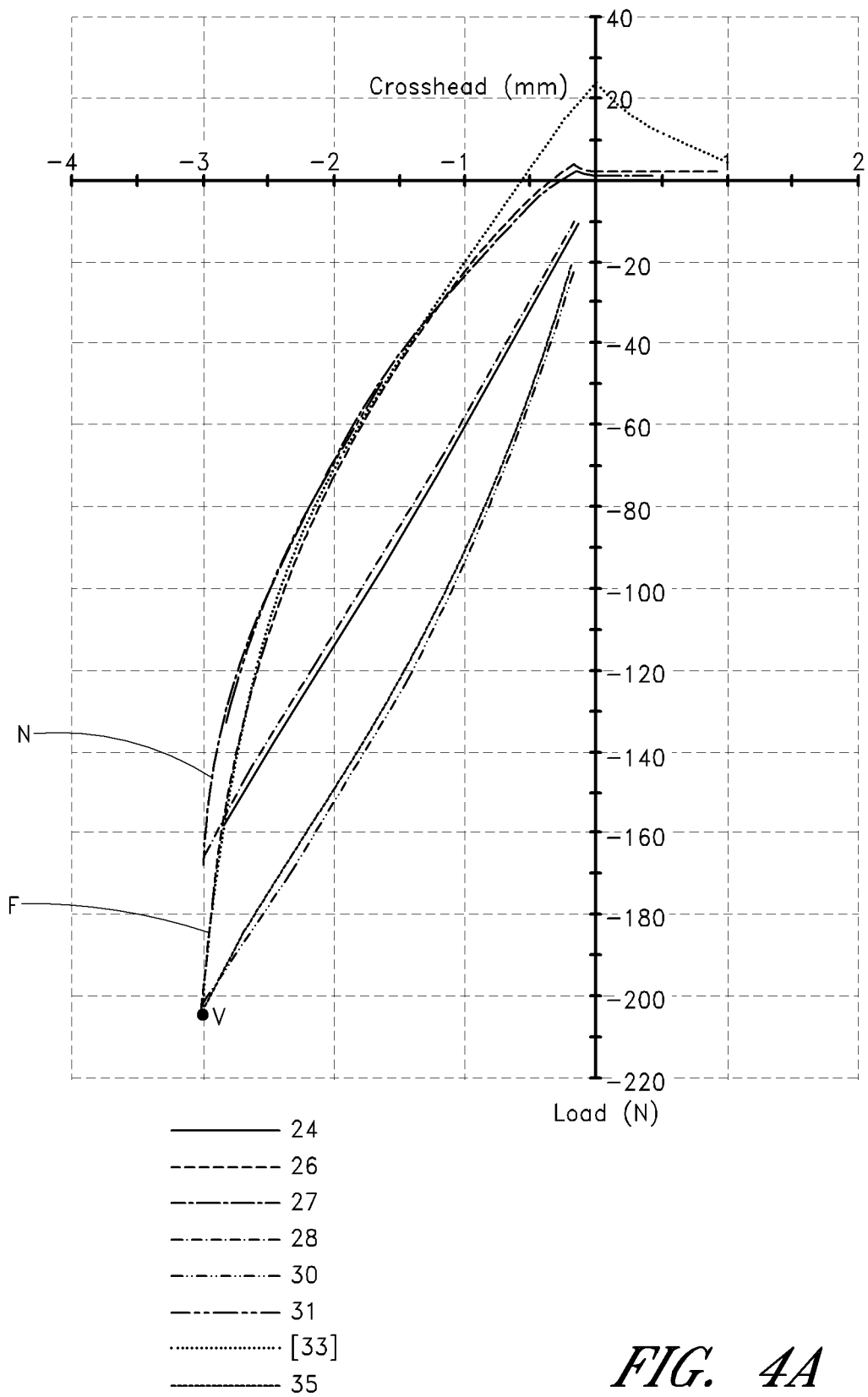

The x-axis shows the displacement (in mm) and the y axis shows the force (in Newtons), from which the spring constant can be derived. FIG. 4 shows, for example, that for sample 6, a force of about 179 N is needed to effect a displacement of about 3 mm when no magnetic flux is present (curve N'), whereas a force of about 200 N is needed to effect the same 3 mm displacement when a magnetic flux is present (curve F'). A MRE spring can have a similar force/displacement performance. Accordingly, the spring constant of the MRE spring can change from about 60 N/mm to about 67 N/mm, or an increase of about 12%, with and without a magnetic flux density of about 0.6 Tesla, respectively. In another embodiment, for sample 2, the spring constant of the MRE spring, such as the MRE spring 75, a force of about 372 N is needed to effect a displacement of about 3 mm when no magnetic flux is present (curve N"), whereas a force of about 434 N is needed to effect the same 3 mm displacement when a magnetic flux is present (curve F"). In this embodiment, the MRE spring can have a spring constant that can change from about 124 N/mm, without a magnetic field present, to about 145 N/mm with a magnetic field present, or an increase of about 17%. In still another embodiment, shown in FIG. 4A, which shows force-displacement curves for different samples 24, 26, 27, 28, 30, 31, 33, 35, a force of about 170 N is needed to effect a displacement of about 3 mm when no magnetic flux is present (curve N), whereas a force of about 210 N is needed to effect the same 3 mm displacement when the magnetic flux is present (curve F). The MRE spring can thus have a spring constant of about 57 N/mm when no magnetic flux is present, and a spring constant of about 70 N/mm when a magnetic flux is present, or an increase of about 23.5%. However, in other embodiments, the spring constant of the MRE spring can be lower (e.g., about 9%) or higher (e.g., about 25%) than the values above and can be achieved, for example, by varying the size and shape of the MRE spring module. Advantageously, such an increase in the stiffness of the MRE spring 75, when incorporated into a prosthetic device, such as the prosthetic foot 100, provides the variable stiffness that allows a user to transition between low activity and high activity levels, with the MRE spring 75 providing the corresponding level of stiffness.

TABLE 4.1

MRE samples and measuring results at 15% strain.

| Sample No. | Matrix Material | CIP Type | Particle Distribution | $F_{off}$ [N] | $F_{on}$ [N] | ΔF [N] | $k_{off}$ [N/mm] | $k_{on}$ [N/mm] | Δk [N/mm] | Δk/$k_{off}$ |
|---|---|---|---|---|---|---|---|---|---|---|
| 1 | Silicone | CM | Aligned | 375 | 414 | 39 | 125 | 138 | 13 | 10% |
| 2 | Silicone | CM | Aligned | 372 | 434 | 62 | 124 | 145 | 21 | 17% |
| 3 | Silicone | CM | Aligned | 365 | 408 | 43 | 122 | 136 | 14 | 12% |
| 4 | Silicone | CM | Aligned | 334 | 370 | 36 | 111 | 123 | 12 | 11% |
| 5 | Silicone | CM | Aligned | 249 | 295 | 46 | 83 | 98 | 15 | 19% |
| 6 | Silicone | CM | Isotropic | 179 | 200 | 21 | 60 | 67 | 7 | 12% |
| 7 | Silicone | CM | Isotropic | 201 | 203 | 2 | 67 | 68 | 1 | 0% |
| 8 | Silicone | CC | Aligned | 209 | 248 | 39 | 70 | 83 | 13 | 19% |
| 9 | PU | CM | Aligned | 636 | 695 | 59 | 212 | 232 | 20 | 9% |
| 10 | PU | CM | Aligned | 335 | 373 | 38 | 112 | 124 | 12 | 11% |
| 11 | PU | CM | Aligned | 416 | 448 | 32 | 139 | 149 | 10 | 8% |
| 12 | PU | CM | Aligned | 553 | 606 | 53 | 184 | 202 | 18 | 10% |
| 13 | PU | CC | Aligned | 491 | 591 | 100 | 164 | 197 | 33 | 20% |
| 14 | PU | CC | Aligned | 437 | 548 | 111 | 146 | 183 | 37 | 25% |
| 15 | PU | CC | Aligned | 293 | 318 | 25 | 98 | 106 | 8 | 9% |
| 16 | PU | CC | Aligned | 363 | 442 | 79 | 121 | 147 | 26 | 22% |
| 17 | PU | CC | Isotropic | 354 | 412 | 58 | 118 | 137 | 19 | 16% |

Figure 5A:
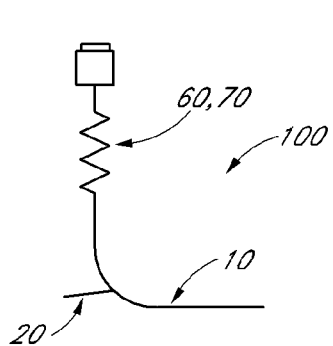
FIG. 5A-5G are schematic side views of several embodiments of prosthetic foot designs with one or more MRE springs.

FIGS. 5A-G show additional embodiments of prosthetic devices that incorporate a spring module, such as the spring module 70 with the MRE spring 75 described above. FIG. 5A is a schematic side view of the prosthetic foot 100 described above.

Figure 5B:
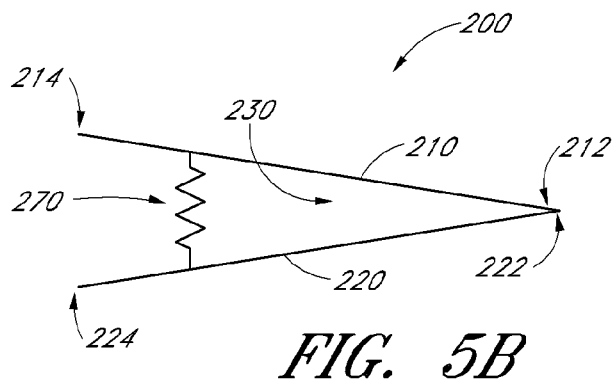

FIG. 5B is a schematic side view of another embodiment of a prosthetic foot 200. The prosthetic foot 200 has a generally planar upper member 210 and a generally planar lower member 220 disposed below the upper member 210. In the illustrated embodiment, the front ends 212, 222 of the upper and lower members 210, 220 can be attached to each other, and the rear ends 214, 224 of the upper and lower members 210, 220 can be spaced apart from each other, such that the members 210, 220 define a lengthwise slot 230 in the fore-aft direction between the members 210, 220. With continued reference to FIG. 5B, the slot 230 can taper toward the front ends 212, 222. In one embodiment, an adapter (not shown) can be coupled to the upper member 210 proximate its rear end 214 to allow the prosthetic foot 200 to be operatively attached to a socket.

In one embodiment, the lower member 220 can be a sole portion of the prosthetic foot 200 that contacts the ground during ambulation, and the upper member 201 can include an ankle section of the prosthetic foot 200. A MRE spring module 270 can be disposed between the upper member 210 and the lower member 220 (e.g., at a rear portion of the prosthetic foot 200), where the MRE spring module 270 can be selectively actuated to vary its stiffness, thereby varying the amount that the upper member 210 displaces toward the lower member 220 during ambulation of the prosthetic foot 200.

Figure 5C:
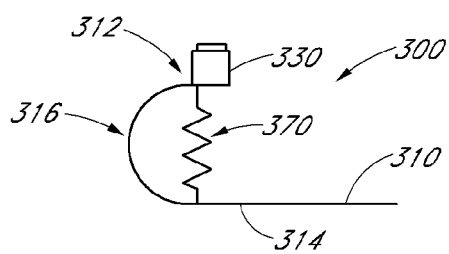

FIG. 5C shows a schematic side view of another embodiment of a prosthetic foot 300. The prosthetic foot 300 has as foot member 310 with a proximal portion 312, a distal portion 314 and an intermediate portion 316. In the illustrated embodiment, the proximal portion 312 and distal portion 314 extend generally horizontally, with the proximal portion 312 disposed above the distal portion 314. In one embodiment, the proximal and/or distal portions 312, 314 can be generally planar. The intermediate portion 316 can be curved and interconnect the proximal portion 312 and the distal portion 314. In the illustrated embodiment, the intermediate portion 316 can be C-shaped. In another embodiment, the intermediate portion 316 can be U-shaped. However, the intermediate embodiments can have other suitable shapes. In one embodiment, the foot member 310 can be monolithic, so that the proximal, distal and intermediate portions 312, 314, 316 form part of a single piece. In another embodiment, the proximal, distal and intermediate portions 312 314, 316 can be separate pieces that attach to each other to define the foot member 310. The intermediate portion 316 can operate like a spring and allow the deflection of the proximal portion 312 relative to the distal portion 314. An adapter 330 can be attached to the proximal portion 312 of the foot member 310, to allow the prosthetic foot 300 to be operatively coupled to a socket (e.g., via a pylon member).

A MRE spring module 370 can be disposed between the proximal portion 312 and the distal portion 314 (e.g., at a rear portion of the prosthetic foot 200). In one embodiment, the MRE spring module 370 is aligned with the adapter 330. The MRE spring module 370 can be selectively actuated to vary its stiffness, and as a result the amount that the proximal portion 312 deflects toward the distal portion 314 during ambulation of the prosthetic foot 300 (e.g., when transitioning from mid-stance to toe-off) can be varied.

Figure 5D:
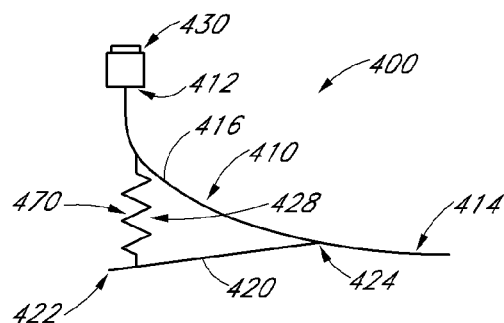

FIG. 5D shows a schematic side view of another embodiment of a prosthetic foot 400. The prosthetic foot 400 can have a first foot member 410 that extends from a generally vertical proximal portion 412 to a generally horizontal distal portion 414, with an intermediate portion 416 that curves downwardly and forwardly from the proximal portion 412 toward the distal portion 414. The prosthetic foot 400 can also have a second foot member 420 disposed below the first foot member 410 at a rear portion of the foot 400, where the second foot member 420 extends from a proximal end 422 at a rear most end of the foot 400 to a distal end 424. In one embodiment, the distal end 424 of the second foot member 420 is adjacent and attached to the first foot member 410 at a location between the proximal and distal portions 412, 414 of the first foot member. In one embodiment, the second foot member 420 can be generally planar or flat along its length. In the illustrated embodiment, the first and second foot members 410, 420 define a slot 428 therebetween in the fore-aft direction. The prosthetic foot can also have an adapter 430 attached to the proximal portion 412.

A MRE spring module 470 can be disposed in the slot 428 between the first and second foot members 410, 420 at a rear portion of the prosthetic foot 400. In the illustrated embodiment, the MRE spring module 470 is disposed axially between the intermediate portion 416 of the first foot member 410 and a location proximate the distal end 422 of the second foot member 420. In one embodiment, the MRE spring module 470 is aligned with the adapter 430. The MRE spring module 470 can be selectively actuated to vary its stiffness, and as a result the amount that the second foot member 420 deflects toward the first foot member 410, for example at heel strike of the prosthetic foot 400 during ambulation, can be varied.

Figure 5E:
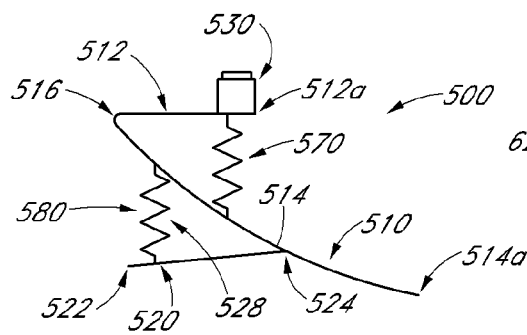

FIG. 5E shows a schematic side view of another embodiment of a prosthetic foot 500. The prosthetic foot 500 can have a first foot member 510 that includes a generally horizontal upper portion 512 and a lower portion 514. The upper portion 512 extends from a distal end 512a to a transition 516 with the lower portion 514. The lower portion 514 curves downwardly and forwardly from the transition 516 to a distal end 514a. In another embodiment, the lower portion 514 can have a curved portion near the transition 516 and a generally horizontal portion near the distal end 514a. In one embodiment, the transition 516 can be v-shaped. In another embodiment, the transition 516 can be U-shaped. The prosthetic foot 500 can also have a second foot member 520 disposed below the first foot member 510 at a rear portion of the foot 500, where the second foot member 520 extends from a proximal end 522 at a rear most end of the foot 500 to a distal end 524. In one embodiment, the distal end 524 of the second foot member 520 is adjacent and attached to the first foot member 510 at a location between the transition 516 and the distal end 514a of the lower portion 514. In one embodiment, the second foot member 520 can be generally planar or flat along its length. In the illustrated embodiment, the first and second foot members 510, 520 define a slot 528 therebetween in the fore-aft direction at a rear portion of the prosthetic foot 500. The prosthetic foot 500 can also have an adapter 530 attached to the upper portion 512 near its distal end 512a.

A first MRE spring module 570 can be disposed generally vertically between the upper portion 512 and the lower portion 514 of the first foot member 510. In one embodiment, the first MRE spring module 570 can be axially aligned with the adapter 530. In the illustrated embodiment, a second MRE spring module 580 can be disposed generally vertically in the slot 528 between the first and second foot members 510, 520 at a rear portion of the prosthetic foot 500. As shown in FIG. 5E, the first MRE spring module 570 contacts the lower portion 514 of the first foot member 510 at a location distal of the location at which the second MRE spring module 580 contacts the first foot member 510. Accordingly, the first and second MRE spring modules 570, 580 act as parallel springs or shock modules. The second MRE spring module 580 can be selectively actuated to vary its stiffness, and as a result the amount that the second foot member 520 deflects toward the first foot member 510, for example at heel strike of the prosthetic foot 500 during ambulation, can be varied. Similarly, the first spring module 570 can be selectively actuated to vary its stiffness, and as a result the amount that the upper portion 512 deflects toward the lower portion 514, for example at mid-stance and toe-off of the prosthetic foot 500 during ambulation, can be varied.

Figure 5F:
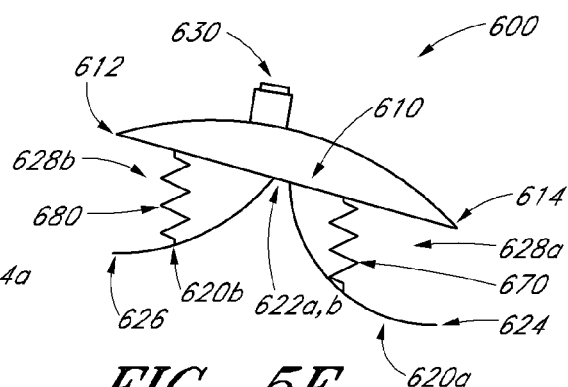

FIG. 5F shows a schematic side view of another embodiment of a prosthetic foot 600. The prosthetic foot 600 includes a foot member 610 that extends between a proximal end 612 and a distal end 614. An adapter 630 can be coupled to an upper surface of the foot member 610 at a location between the proximal and distal ends 612, 614. The prosthetic foot 600 can also have a first lower member 620a and a second lower member 620b disposed below the foot member 610. The first lower member 620a can extend forwardly from a proximal end 622a attached to the foot member 610 to a distal end 624, so as to define a slot 628a in the fore-aft direction between the foot member 610 and the first lower member 620a at a front portion of the prosthetic foot 600. The second lower member 620b can extend rearwardly from a distal end 622b attached to the foot member 610 to a proximal end 626, so as to define a slot 628b in the fore-aft direction between the foot member 610 and the second lower member 620b at a rear portion of the prosthetic foot 600. As shown in FIG. 5F, the first and second lower members 620a, 620b attach to the foot member 610 generally midway between the proximal and distal ends 612, 614 of the foot member 610. In the illustrated embodiment, the first and second lower members 620a, 620b have a generally curved profile. However, the first and second lower members 620a, 620b can have other suitable profiles, such as planar or generally flat.

A first MRE spring module 670 can be disposed generally vertically between the foot member 610 and the first lower member 620a at a front portion of the prosthetic foot 600. A second MRE spring module 680 can be disposed generally vertically between the foot member 610 and the second lower member 620b at a rear portion of the prosthetic foot 600. In one embodiment, one of the MRE spring modules 670, 680 can be axially aligned with the adapter 630. In the illustrated embodiment, the second MRE spring module 680 can be disposed generally vertically in the slot 628b between the foot member 610 and the second lower member 620b at a rear portion of the prosthetic foot 600. As shown in FIG. 5F, the second MRE spring module 680 contacts the foot member 610 at a location distal of the location at which the first MRE spring module 670 contacts the foot member 610. Accordingly, the first and second MRE spring modules 670, 680 act as parallel springs or shock modules. The second MRE spring module 680 can be selectively actuated to vary its stiffness, and as a result the amount that the second lower member 620b deflects toward the foot member 610, for example at heel strike of the prosthetic foot 600 during ambulation, can be varied. Similarly, the first spring module 670 can be selectively actuated to vary its stiffness, and as a result the amount that the first lower member 620a deflects toward the foot member 610, for example at toe-off of the prosthetic foot 600 during ambulation, can be varied.

Figure 5G:
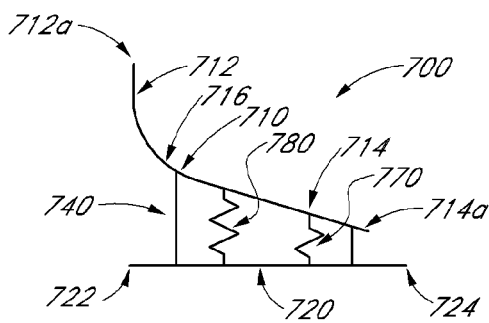

FIG. 5G shows a schematic side view of another embodiment of a prosthetic foot 700. The prosthetic foot 700 can have an upper foot member 710 and a lower foot member 720 disposed below the upper foot member 710. The upper foot member 710 can extend from a proximal portion 712 to a distal portion 714, with an intermediate portion 716 between the proximal and distal portions 712, 714. In the illustrated embodiment, the proximal portion 712 is generally vertical and extends to a proximal end 712a, and the distal portion 714 is generally planar and extends to a distal end 714a. In the illustrated embodiment, the intermediate portion 716 can be curved so that the upper foot member 710 curves downwardly and forwardly from the proximal portion 712 to the distal portion 714. The upper foot member 710 can be a single monolithic piece. In another embodiment, the upper foot member 710 can be modular, with the proximal, intermediate and distal portions 712, 716, 714 being separate pieces that attach to each other. An adapter (not shown) can be attached to the proximal portion 712 of the upper foot member 710.

The lower foot member 720 can extend between a proximal end 722 and a distal end 724. In one embodiment, the lower foot member 720 can extend along a length generally corresponding to the length between the heel and toes of a natural human foot. As shown in FIG. 5G, the distal end 724 of the lower foot member 720 can be disposed forwardly of the distal end 714a of the upper foot member 710, and the proximal end 722 of the lower foot member 720 can be generally aligned with the proximal end 712a of the upper foot member 710. However, in other embodiments, the distal end 724 of the lower foot member 720 can be aligned with the distal end 714a of the upper foot member and/or the proximal end 722 of the lower foot member 720 can be disposed rearwardly of the location of the proximal end 712a of the upper foot member 710. In still another embodiment, the proximal and distal ends 722, 724 of the lower foot member 720 can extend rearwardly and forwardly, respectively, of the proximal and distal ends 712a, 714a of the upper foot member 710. In the illustrated embodiment, the lower foot member 720 is generally planar or flat between the proximal and distal ends 722, 724. In another embodiment, at least a portion of the lower foot member 720 can be curved. For example, the lower foot member 720 can have an arch portion, such as the arch 28 described above in connection with the prosthetic foot 100.

The prosthetic foot 700 can also have an ankle block 740 interposed between and completely separating the upper foot member 710 and lower foot member 720. In one embodiment, the ankle block 740 can be made of an inert elastic material and/or resilient material (e.g., urethane, natural or synthetic rubber, compressible foam such as expanded polyurethane foam or cellular foam) having desired compliance and energy return characteristics. Further information on prosthetic foot designs with ankle blocks can be found in U.S. Pat. Nos. 6,206,934; 6,280,479; and 6,899,737, the entire contents of all of which are hereby incorporated by reference and should be considered a part of this specification.

The prosthetic foot 700 can also include a first MRE spring module 770 and a second MRE spring module 780 disposed between and in contact with the upper foot member 710 and lower foot member 720. In the illustrated embodiment, the first MRE spring module 770 can be disposed between the lower foot member 720 and the distal portion 714 of the upper foot member 710 at a front portion of the prosthetic foot 700. The second MRE spring module 780 can be disposed generally between the lower foot member 720 and the intermediate portion 716 of the upper foot member 710 at a mid-portion of the prosthetic foot 700. In one embodiment, the second MRE spring module 780 can be disposed so that it aligns with the proximal portion 712 of the upper foot member 710. With continued reference to FIG. 5G, the first and second MRE spring modules 770, 780 can be disposed in the ankle block 740. In one embodiment, the MRE spring modules 770, 780 can be embedded in the ankle block 740. In another embodiment, the MRE spring modules 770, 780 can be disposed in openings or cavities within the ankle block 740. Accordingly, the first and second MRE spring modules 770, 780 act as parallel springs or shock modules. The second MRE spring module 780 can be selectively actuated to vary its stiffness, and as a result the amount that the lower foot member deflects toward the upper foot member 710, for example at heel strike or mid-stance of the prosthetic foot 700 during ambulation, can be varied. Similarly, the first MRE spring module 770 can be selectively actuated to vary its stiffness, and as a result the amount that the lower foot member 720 deflects toward the upper foot member 710, for example at toe-off of the prosthetic foot 700 during ambulation, can be varied.

The prosthetic foot embodiments discussed above in connection with FIGS. 5A-G include various foot members (e.g., upper/lower foot members, heel member). In one embodiment, the foot members can have a substantially rectangular transverse cross-section with a generally linear (e.g., not curved) upper edge and lower edge. In another embodiment, the foot members can include two or more longitudinal members separated along at least a portion of their length by a longitudinal slot, such as the members 16a 16b and slot 17 described above in connection with the prosthetic foot 100. Where the prosthetic foot device includes multiple MRE spring modules, actuation of the multiple spring modules can be controlled together (e.g., via one controller) so as to provide a smooth rollover to the prosthetic foot during ambulation.

Figure 6A:
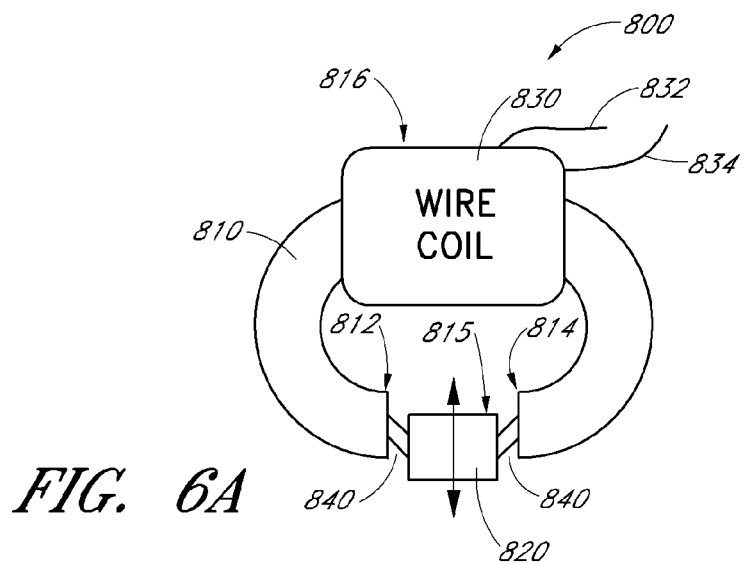
FIGS. 6A-6C re schematic views of several embodiments of a MRE spring element.

FIG. 6A shows a schematic view of one embodiment of a MRE spring module 800. The MRE spring module 800 can have a first component 810 coupled to a second component 820 by MR elastomer portions 840. In the illustrated embodiment, the first component 810 is c-shaped and has spaced apart ends 812, 814 that define an opening 815 therebetween. In another embodiment, the first components can be u-shaped. The first component 810 can be a magnetic core. The second component 820 can be shaped like a block and movably extend in the opening between the spaced apart ends 812, 814. The MR elastomer portions 840 are disposed on either side of the second component 820 between the second component 820 and the ends 812, 814 of the first component. As shown in FIG. 6A, a wire coil 830 is disposed about a central portion 816 of the first component 810 at a location aligned with the second component 820, and electrical connections 832, 834 connect the wire coil 830 to a power source (not shown).

As discussed above, a current can be applied to the MRE spring module 800 (e.g., via electrical connections 832, 834), which generates a magnetic flux. The MR elastomer portions 840 can have ferromagnetic particles interspersed within an elastomeric matrix in a manner whereby the MRE spring module 800 operates in shear when the magnetic flux is applied. For example the properties (e.g., stiffness) of the MR elastomer portions 840 can change in the presence of the magnetic flux so that the second component 820 moves into and out of the opening 815 between the ends 812, 814 of the first component 810. In one embodiment, the MRE spring module 800 can be incorporated into a prosthetic device, such as a prosthetic foot, where the first component 810 is coupled to one member of the prosthetic device and the second component 820 is coupled to another member of the prosthetic device. Accordingly, actuation of the MRE spring module 800 can vary the relative movement of the members of the prosthetic device.

Figure 6B:
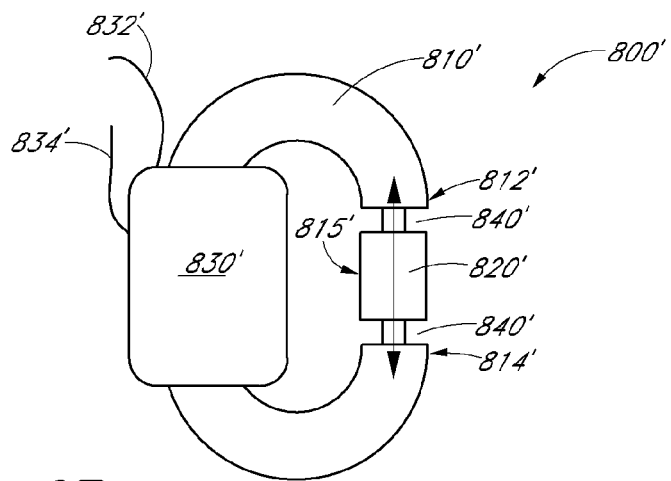

FIG. 6B is a schematic view of another embodiment of a MRE spring module 800'. The MRE spring module 800' is similar to the MRE spring module 800, except as noted below. Thus, the reference numerals used to designate the various components of the MRE spring module 800' are identical to those used for identifying the corresponding components of the MRE spring module 800 in FIG. 6A, except that a "'" has been added to the reference numerals.

The MRE spring module 800' can have a first component 810' and a second component 820' that are interconnected by MR elastomer portions 840'. The first component 810' can be c-shaped and have a wire coil 830' disposed about an intermediate portion 816' of the first component 810' at a location generally aligned with the second component 820', and electrical connections 832', 834' connect the wire coil 830' to a power source (not shown). However, the first component 810' can have other suitable shapes, such as a u-shape. The first component 810' can function as a magnetic core. The second component 820' can be shaped like a block and movably extend in an opening 815' between spaced apart ends 812', 814' of the first component 810'. The MR elastomer portions 840' are disposed on either side of the second component 820' between the second component 820' and the ends 812', 814' of the first component.

With continued reference to FIG. 6B, the MR elastomer portions 840' can have ferromagnetic particles interspersed within an elastomeric matrix in a manner whereby the MRE spring module 800' operates in tension and compression when a magnetic flux is applied to the spring module 800'. For example the properties (e.g., stiffness) of the MR elastomer portions 840' can change in the presence of the magnetic flux so that the ends 812', 814' of the first component 810' move toward or away from the second component 820'. In one embodiment, the MRE spring module 800' can be incorporated into a prosthetic device, such as a prosthetic foot, where the first component 810' is coupled to one member of the prosthetic device and the second component 820' is coupled to another member of the prosthetic device. Accordingly, actuation of the MRE spring module 800' can vary the relative movement of the members of the prosthetic device, and the stiffness of the prosthetic device.

Figure 6C:
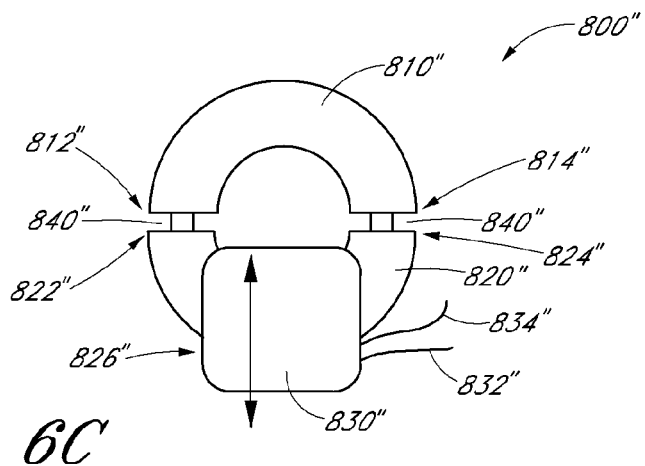

FIG. 6C is a schematic view of another embodiment of a MRE spring module 800". The MRE spring module 800" is similar to the MRE spring module 800, except as noted below. Thus, the reference numerals used to designate the various components of the MRE spring module 800" are identical to those used for identifying the corresponding components of the MRE spring module 800 in FIG. 6C, except that a "″" has been added to the reference numerals.

The MRE spring module 800" can have a first component 810" and a second component 820" that are interconnected by MR elastomer portions 840". The first component 810" can be c-shaped. However, the first component 810" can have other suitable shapes, such as a u-shape. The first component 810" can function as a magnetic core. The second component 820" can be c-shaped with ends 822", 824" that are disposed opposite ends 812", 814" of the first component 810" so that the first and second components 810", 820" face each other. A wire coil 830" can be disposed about an intermediate portion 826" of the second component 820', and electrical connections 832", 834" connect the wire coil 830" to a power source (not shown). In another embodiment, the second component 820" can be u-shaped. The MR elastomer portions 840" are disposed between the ends 812", 814" of the first component 810" and the ends 822", 824" of the second component 820".

With continued reference to FIG. 6C, the MR elastomer portions 840" can have ferromagnetic particles interspersed within an elastomeric matrix in a manner whereby the MRE spring module 800" operates only in compression when a magnetic flux is applied to the spring module 800". For example the properties (e.g., stiffness) of the MR elastomer portions 840" can change in the presence of the magnetic flux so that the ends 812", 814" of the first component 810" move toward the ends 822", 824" of the second component 820". In one embodiment, the MRE spring module 800" can be incorporated into a prosthetic device, such as a prosthetic foot, where the first component 810" is coupled to one member of the prosthetic device and the second component 820" is coupled to another member of the prosthetic device. Accordingly, actuation of the MRE spring module 800" can vary the stiffness of the members of the prosthetic device.

As described in the embodiments above, a magnetorheological elastomer (MRE) spring element can be placed in various locations of any variation of a prosthetic or orthotic device. By choosing the location of one or more MRE spring elements, relative to the device's structure, the spring elements could, for example, provide variable stiffness for heel-strike, toe-off, or in general shock absorption for the prosthetic or orthotic device. Additionally, the design and structure of the MRE spring element can vary, with MR elastomers that can be used in one or more of compression, tension and shear.

Accordingly, the embodiments above disclose orthotic and prosthetic devices where the stiffness of the device is controllable and adaptable to the user's current activity level. The device can be controlled either manually or automatically by responding to signals that represent the current activity level of the user, and be able to change its operating characteristics (e.g., stiffness) in real-time.

Of course, the foregoing description is that of certain features, aspects and advantages of the present invention, to which various changes and modifications can be made without departing from the spirit and scope of the present invention. Moreover, the prosthetic or orthotic device with the MRE spring need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of the specific features and aspects between and among the different embodiments may be made and still fall within the scope of the invention. Accordingly, it should be understood that various features and aspects of the disclosed embodiments can be combined with or substituted for one another in order to form varying modes of the discussed prosthetic or orthotic device having MRE springs.

What is claimed is:

1. A method of using a prosthetic or orthotic device, comprising:
    coupling a shock absorption member to at least a portion of a human limb, the shock absorption member comprising one or more magnetorheological elastomer springs and a coil, the one or more magnetorheological elastomer springs and the coil both disposed circumferentially around a core, the coil disposed radially between the one or more magnetorheological elastomer springs and the core, wherein a central vertical axis of the shock absorption member is vertically aligned with a central vertical axis of a coupling mechanism for coupling the shock absorption member to the at least a portion of a human limb;
    moving the core only axially based on a first applied force;
    applying a magnetic flux to the one or more magnetorheological elastomer springs by magnetizing an upper disc coupled to the one or more magnetorheological elastomer springs to alter the stiffness of the one or more magnetorheological elastomer springs; and
    moving the core only axially based on a second applied force after altering the stiffness of the one or more magnetorheological elastomer springs.

2. The method of claim 1, wherein applying a magnetic flux comprises actuating the coil to induce a magnetic flux.

3. The method of claim 1, wherein applying a magnetic flux comprises applying electrical current through the coil.

4. The method of claim 1, wherein applying a magnetic flux comprises magnetizing the core.

5. A method of using a prosthetic or orthotic device, comprising:
    coupling a shock absorption member to at least a portion of a human limb, the shock absorption member comprising one or more magnetorheological elastomer springs and a coil, the one or more magnetorheological elastomer springs and the coil both disposed circumferentially around a core, the coil disposed radially between the one or more magnetorheological elastomer springs and the core, wherein a central vertical axis of the shock absorption member is vertically aligned with a central vertical axis of a coupling mechanism for coupling the shock absorption member to the at least a portion of a human limb;
    moving the core only axially based on a first applied force;
    applying a magnetic flux to the one or more magnetorheological elastomer springs by magnetizing a lower disc coupled to the one or more magnetorheological elastomer springs to alter the stiffness of the one or more magnetorheological elastomer springs; and
    moving the core only axially based on a second applied force after altering the stiffness of the one or more magnetorheological elastomer springs.

6. The method of claim 1, wherein applying a magnetic flux comprises magnetizing a lower disc coupled to the one or more magnetorheological elastomer springs.

7. A method of using a prosthetic or orthotic device, comprising:
    coupling a shock absorption member to at least a portion of a human limb, the shock absorption member comprising a magnetorheological elastomer spring, a core, and a coil disposed circumferentially around the core and radially between the one or more magnetorheological elastomer springs and the core, wherein a central vertical axis of the shock absorption member is vertically aligned with a central vertical axis of a coupling mechanism for coupling the shock absorption member to the at least a portion of a human limb;

moving the core axially within a linear bearing; and
applying a magnetic flux to the magnetorheological elastomer spring by magnitizing an upper disc coupled to the linear bearing to alter the stiffness of the magnetorheological elastomer spring.

8. The method of claim 7, wherein applying a magnetic flux comprises actuating a coil to induce the magnetic flux.

9. The method of claim 7, wherein applying a magnetic flux comprises applying electrical current through the coil.

10. The method of claim 7, wherein applying a magnetic flux comprises magnitizing the core.

11. A method of using a prosthetic or orthotic device, comprising:
coupling a shock absorption member to at least a portion of a human limb, the shock absorption member comprising a magnetorheological elastomer spring, a core, and a coil disposed circumferentially around the core and radially between the one or more magnetorheological elastomer springs and the core, wherein a central vertical axis of the shock absorption member is vertically aligned with a central vertical axis of a coupling mechanism for coupling the shock absorption member to the at least a portion of a human limb;
moving the core axially within a linear bearing; and
applying a magnetic flux to the magnetorheological elastomer spring by magnitizing a lower disc coupled to the core to alter the stiffness of the magnetorheological elastomer spring.

12. A method of using a prosthetic or orthotic device, comprising:
coupling a shock absorption member to at least a portion of a human limb, the shock absorption member comprising a magnetorheological elastomer spring, a core, and a coil disposed circumferentially around the core and radially between the one or more magnetorheological elastomer springs and the core, wherein a central vertical axis of the shock absorption member is vertically aligned with a central vertical axis of a coupling mechanism for coupling the shock absorption member to the at least a portion of a human limb;
moving the core axially within a linear bearing; and
applying a magnetic flux to the magnetorheological elastomer spring by magnitizing an upper disc and a lower disc to alter the stiffness of the magnetorheological elastomer spring, the upper disc and the lower disc coupled to the magnetorheological elastomer spring.

* * * * *